United States Patent [19]

Walker, Jr.

[11] Patent Number: 5,292,947

[45] Date of Patent: Mar. 8, 1994

[54] PROCESS FOR PREPARING ALKYLSULFONIC ANHYDRIDES

[75] Inventor: Theodore R. Walker, Jr., Kingsport, Tenn.

[73] Assignee: Eastman Kodak Company, Rochester, N.Y.

[21] Appl. No.: 952,228

[22] Filed: Sep. 28, 1992

[51] Int. Cl.⁵ .............. C07C 303/22; C07C 303/00; C07C 45/00
[52] U.S. Cl. ...................... 562/872; 568/309
[58] Field of Search ......................... 562/872

[56] References Cited

U.S. PATENT DOCUMENTS

| | | | |
|---|---|---|---|
| 2,489,316 | 11/1949 | Pruell | 562/872 |
| 3,829,484 | 8/1974 | Sowerby et al. | 562/872 |
| 5,004,829 | 4/1991 | Aramaki et al. | 562/113 |
| 5,107,029 | 4/1992 | Walker, Jr. et al. | 568/319 |

FOREIGN PATENT DOCUMENTS 262919 4/1988 European Pat. Off. .
672640 9/1947 United Kingdom .

OTHER PUBLICATIONS

L. N. Owen et al., *J. Chem. Soc.*, p. 3723 (1953).
R. C. Paul et al., *Chemistry and Industry*, 25, p. 702 (1971).
W. Dabkowski et al., *Chem. Ber.*, 118, pp. 1809–1824 (1985).
E. A. Robinson et al., *Canadian Journal of Chemistry*, 44, pp. 1437–1444 (1966).

*Primary Examiner*—José G. Dees
*Assistant Examiner*—Dwayne C. Jones
*Attorney, Agent, or Firm*—Betty J. James; William P. Heath, Jr.

[57] ABSTRACT

This invention relates to a process for preparing an alkylsulfonic anhydride comprising contacting
(A) a dehydrated phosphoric acid with
(B) an alkylsulfonic acid having 1 to 6 carbon atoms, under conditions of temperature and pressure to result in the substituted absence of phosphoric/alkylsulfonic mixed anhydride and production of a mixture of alkylsulfonic acid and its corresponding anhydride at a conversion of at least 10% of alkylsulfonic acid to the corresponding alkylsulfonic anhydride.

10 Claims, No Drawings

PROCESS FOR PREPARING ALKYLSULFONIC ANHYDRIDES

FIELD OF THE INVENTION

This invention relates to a process for preparing alkylsulfonic anhydrides, and optionally diketones.

BACKGROUND OF THE INVENTION

Methanesulfonic anhydride finds many applications in the synthesis of certain methyl sulphonates. In the prior art process of L. N. Owen & Whitelaw, S. P., described in *J. Chem. Soc.*, p 3723 (1953), methanesulfonic anhydride was prepared by refluxing methanesulfonic acid with thionyl chloride for 3 hours, resulting in a crude product.

In another prior art process, methanesulfonic acid was mixed with phosphorus oxide at certain conditions by R. C. Paul, S. K. Sharma, R. D. Sharma and K. C. Malhotra as described in *Chemistry and Industry*, page 702, June 17, 1991.

SUMMARY OF THE INVENTION

This invention relates to a process for preparing an alkylsulfonic anhydride comprising contacting (A) a dehydrated phosphoric acid with
(B) an alkylsulfonic acid having 1 to 6 carbon atoms, under conditions of temperature and pressure to result in the absence of phosphoric/alkylsulfonic mixed anhydride and production of a mixture of alkylsulfonic acid and its corresponding anhydride at a conversion of at least 10% of said alkylsulfonic acid to the corresponding alkylsulfonic anhydride.

The invention also relates to a process comprising:

(I) heating phosphoric acid at about 200° to about 300° for about 20 to about 300 minutes and removing water produced by vacuum distillation to form dehydrated phosphoric acid;

(II) contacting
 (A) dehydrated phosphoric acid produced from step (I) with
 (B) an alkylsulfonic acid having 1 to 6 carbon atoms, under conditions of temperature and pressure to result in the absence of phosphoric/alkylsulfonic mixed anhydride and production of a mixture of alkylsulfonic acid and its corresponding anhydride at a conversion of at least 10% of said alkylsulfonic acid to the corresponding alkylsulfonic anhydride, and (III) separating the mixture of alkylsulfonic acid and its corresponding anhydride from phosphoric acid by distillation.

It is preferred to add the step of contacting the mixture of alkylsulfonic acid and its corresponding anhydride produced by step (III) with an aromatic diacid containing 8 to 30 carbon atoms and a non-diacid polynuclear aromatic hydrocarbon containing 10 to 30 carbon atoms to produce a diketone.

Some of the advantages of the invention include easier regeneration for recycling and less expense as compared to prior art methods for preparing alkylsulfonic anhydride.

DETAILED DESCRIPTION OF THE PREFERRED EMBODIMENTS

This invention relates to a process for preparing an alkylsulfonic anhydride comprising contacting a dehydrated phosphoric acid with (B) an alkylsulfonic acid having from about 1 to about 6 carbon atoms. The phosphoric acid can be dehydrated by any method known to one skilled in the art. Preferably, the phosphoric acid is heated at 180° C. 300° C., more preferably under vacuum. Water is distilled away to give mildly dehydrated phosphoric acid. The alkylsulfonic acid may be purchased, synthesized, or recovered from polyketone monomer preparation known to one skilled in the art. U.S. Pat. No. 5,107,029, incorporated herein by reference in its entirety, discloses a supernatent aqueous layer which is a mixture of water and methanesulfonic acid and which may be isolated by distillation. Other ways of making the polyketone monomer are listed in U.S. Pat. No. 5,107,029 at column 1. The alkylsulfonic acid is added to the phosphoric acid. The resulting alkylsulfonic acid/alkylsulfonic anhydride mixture is distilled under vacuum.

Although alkylsulfonic acid and alkylsulfonic anhydride may be separated during this distillation, it is not necessary since they will be mixed again in the preparation of more monomer. The undistilled phosphoric acid remaining in the reactor is recycled by heating under vacuum to dehydrate it.

The steps involved in this process are:

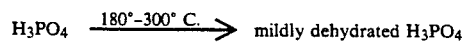

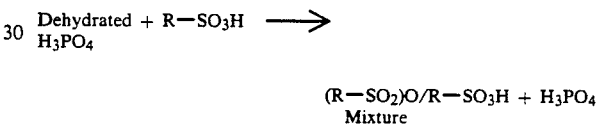

It is preferred that the following step is added:

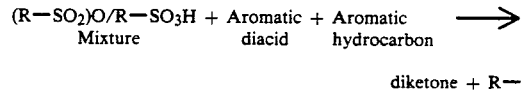

The alkylsulfonic acid may be any straight-chain, branched-chain, or cyclic aliphatic sulfonic acid. Aromatic sulfonic anhydrides may also be made by this process, but they are not useful for making polyketone monomers because they are so reactive that they produce undesirable by-products.

The preferred alkylsulfonic acids are methane sulfonic acid and 1,2-ethanedisulfonic acid. The latter produces a cyclic anhydride by the process of this invention. The more preferred alkylsulfonic acid is methanesulfonic acid.

Optionally, the process can contain an additional step of contacting the mixture of alkylsulfonic acid and its corresponding anhydride with an aromatic diacid containing 8 to 30 carbon atoms and a non-diacid polynuclear aromatic hydrocarbon containing 10 to 30 carbon atoms to produce a diketone.

Useful diketones that can be prepared by the process of this invention include

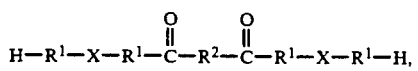

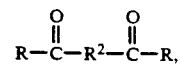

-continued

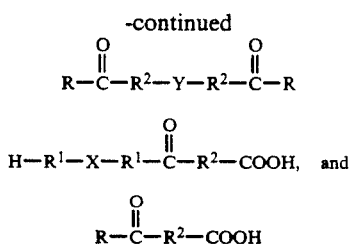

wherein
each $R^1$ is, independently,
(a) a phenylene moiety optionally substituted with up to three substituents selected from the group consisting of lower alkyl and lower alkoxy,
(b) a naphthylene moiety optionally substituted with up to six substituents selected from the group consisting of lower alkyl and lower alkoxy, or
(c) a biphenylene moiety optionally substituted with up to eight substituents selected from the group consisting of lower alkyl and lower alkoxy, each $R^2$ is, independently, $R^3$ or $R^4$,
each $R^3$ is, independently,
(a) a phenylene moiety optionally substituted with up to three substituents selected from the group consisting of lower alkyl, lower alkoxy, halo, hydroxy, acyl, perfluoroalkyl, cyano, nitro, dialkylamino, and acylamino,
(b) a naphthalene moiety optionally substituted with up to six substituents selected from the group consisting of lower alkyl, lower alkoxy, halo, hydroxy, acyl, perfluoroalkyl, cyano, nitro, dialkylamino, and acylamino, or
(c) a biphenylene moiety optionally substituted with up to eight substituents selected from the group consisting of lower alkyl, lower alkoxy, halo, hydroxy, acyl, perfluoroalkyl, cyano, nitro, dialkylamino, and acylamino, each $R^4$ is, independently,
(a) a linear or branched aliphatic moiety containing 3 to 20 carbon atoms optionally substituted with up to 4 substituents selected from the group consisting of lower alkyl, lower alkoxy, halo, hydroxy, acyl, perfluoroalkyl, cyano, nitro, dialkylamino, and acylamino, or
(b) a cycloaliphatic moiety containing 3 to 20 carbon atoms optionally substituted with up to 4 substituents selected from the group consisting of lower alkyl, lower alkoxy, halo, hydroxy, acyl, perfluoroalkyl, cyano, nitro, dialkylamino, and acylamino, X is a direct bond, O, S, or —CH=CH—;
Y is a direct bond, O, S,

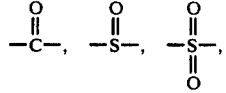

—CH=CH— or —O—$R^2$—O—; and
R is the residue of a polynuclear hydrocarbon after removal of a hydrogen atom and contains at least 10 carbon atoms (i.e., is a residue of reactant (B)).

By "aromatic diacid" we mean all of those disclosed in British Patent 2,166,990, incorporated herein by reference in its entirety. Additionally, other aromatic dicarboxylic acids which are not disclosed in British Patent 2,166,990 are also useful in the process of the invention. Such dicarboxylic acids include those having the general formula HOOC—$R^3$—COOH, where —$R^3$— is as defined hereinabove and the —COOH moieties are directly bonded to an aromatic ring and are separated from each other by at least three carbon atoms. Other suitable dicarboxylic acids have the general formula HOOC—$R^3$—Y—$R^3$—COOH wherein —Y— and —$R^3$—, independently, are as defined hereinabove. It is preferred that the aromatic moiety or moieties are unsubstituted.

Examples of useful aromatic diacids are ones selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid; and said non-diacid polynuclear aromatic hydrocarbon is selected from the group consisting of diphenyl ether, diphenyl sulfide, dibenzofuran, biphenyl, naphthalene, anthracene, dibenzo-p-dioxin, fluorene, xanthane, and phenanthrene.

By non-diacid polynuclear aromatic hydrocarbon, we mean all of those disclosed in British Patent 2,116,990 and U.S. Pat. No. 4,611,033 plus other compounds having the general formulae H—$R^1$—X—$R^1$—H or H—$R^5$—H, wherein each $R^1$, independently, and X are as defined hereinabove and $R^5$ is a polynuclear hydrocarbon moiety. Examples of $R^5$ moieties are those having 2, 3 or 4 fused rings, each of which is preferably aromatic, wherein the $R^5$ moiety is optionally substituted with up to 8 substituents such as with lower alkyl and/or lower alkoxy groups. Each of the fused rings of the $R^5$ moiety may also optionally contain 1, 2 or 3 hetero atoms such as O, N, S, and/or P. Preferred are unsubstituted, non-heterocyclic $R^5$ moieties wherein all rings are aromatic.

A solvent may be used to aid the dehydration of phosphoric acid. Azeotrope may be used.

An unreactive solvent may be used in the production of alkylsulfonic anhydride from alkylsulfonic acid and dehydrated phosphoric acid.

Examples of useful solvents are deactivated aromatic solvents such as nitrobenzene, diphenyl sulfone, and benzophenone. Aromatic solvents are defined herein as solvents that are deactivated by an electron-withdrawing group react with alkylsulfonic acids and anhydrides to produce undesirable methyl sulfones. However, it is preferred that no solvent is used.

The production of alkylsulfonic anhydride from alkylsulfonic acid and dehydrated phosphoric acid is preferably conducted under reduced or negative pressure so that alkylsulfonic anhydride (which is high boiling) may be distilled as it forms. The pressure useful in the process of this invention is preferably less than 20 mm Hg, more preferably less than 10 mm Hg, more preferably less than 5 mm Hg, and even more preferably, less than 1 mm Hg.

The temperature range useful within the context of this invention is from about 180° C. to about 300° C. The preferred temperature range is 200° C. to 250° C.

The conditions of temperature and pressure useful in the process of the invention are such that they should result in the substituted absence of phosphoric/alkylsulfonic mixed anhydride and production of a mixture of alkylsulfonic acid and its corresponding anhydride at a conversion of at least 10% of said alkylsulfonic acid to the corresponding alkylsulfonic anhydride. It is preferred that the conversion of alkylsulfonic acid to the corresponding alkylsulfonic anhydride is at least about 20%.

It is also preferred that the dehydrated phosphoric acid is prepared by heating phosphoric acid at about 180° C. to about 300° C. for about 20 minutes to about 300 minutes, and more preferably, from about 20 to about 180 minutes and then removing water produced by vacuum distillation or by other distillation processes known in the art.

Concentration is not important to the process of this invention. It is only necessary to have enough dehydrated phosphoric acid present to produce the needed amount of anhydride. A large excess of dehydrated phosphoric acid may be used or a large excess of methanesulfonic acid may be used.

It is preferred that the process of the invention be performed continuously so that the alkylsulfonic acid and phosphoric acid are recycled.

This invention can be further illustrated by the following examples of preferred embodiments thereof, although it will be understood that these examples are included merely for purposes of illustration and are not intended to limit the scope of the invention unless otherwise specifically indicated. The starting materials are commercially available unless otherwise noted. All percentages are by weight unless otherwise noted.

EXAMPLE 1

This example illustrates the use of $H_3PO_4$ to produce alkylsulfonic acid.

Phosphoric acid (85%), 500 g, is placed in a distillation apparatus equipped with a 12-inch Vigreux column. The acid is heated for 2 hours at 220°–240° C. under 1.0 mm Hg pressure. The water evolved is collected in a trap cooled by dry ice. Afterwards, 672 g (7 moles) methanesulfonic acid is added and methanesulfonic anhydride/acid mixture is distilled (150°–160° C. at 3 mm Hg) to give 226 g distillate containing 39% methanesulfonic anhydride and 61% methanesulfonic acid. A later fraction, 351 g, of pure methanesulfonic acid is also obtained. The yield of methanesulfonic anhydride is 121 g.

EXAMPLE 2

This example illustrates the use of recycled $H_3PO_4$ to produce alkylsulfonic acid.

The undistilled bottoms from Example 1, containing $H_3PO_4$, is heated for 2 hours at 220°–250° C. and 0.5–1.0 mm Hg pressure. Water is collected in a trap containing isopropyl alcohol. The trap is topped by a condenser cooled with dry ice.

Methanesulfonic acid, 686 g (7.14 moles), is added and a mixture of methanesulfonic anhydride/acid is distilled to give:

|            | Weight | Anhydride | Acid |
|------------|--------|-----------|------|
| Fraction 1 | 130 g  | 64%       | 36%  |
| Fraction 2 | 199 g  | 26%       | 74%  |

The total yield of anhydride is 177 g.

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

I claim:

1. A process for preparing an alkylsulfonic anhydride comprising
   contacting
   (A) a dehydrated phosphoric acid with
   (B) an alkylsulfonic acid having 1 to 6 carbon atoms,
   under conditions of temperature from about 180° C. to about 300° C. and press less than 20 mm Hg to result in the absence of phosphoric/alkylsulfonic mixed anhydride and production of a mixture of alkylsulfonic acid and its corresponding anhydride at a conversion of at least 10% of said alkylsulfonic acid to the corresponding alkylsulfonic anhydride.

2. The process of claim 1 wherein the pressure is less than about 1 mm Hg.

3. The process of claim 1 wherein the alkylsulfonic acid is methanesulfonic acid or 1,2-ethanedisulfonic acid.

4. The process of claim 1 wherein the conversion of alkylsulfonic acid to the corresponding alkylsulfonic anhydride is at least about 20%.

5. The process of claim 1 wherein said dehydrated phosphoric acid is prepared by heating phosphoric acid at about 180° C. to about 300° C. for about 20 to about 300 minutes and removing water produced by vacuum distillation.

6. The process of claim 5 wherein dehydration of phosphoric acid is performed under a negative pressure.

7. The process of claim 1 followed by the additional step of separating the mixture of alkylsulfonic acid and its corresponding anhydride from phosphoric acid by distillation.

8. The process of claim 1 followed by the additional steps of separating the alkylsulfonic acid from its corresponding anhydride by distillation.

9. A process comprising:
   (I) heating phosphoric acid at about 180° to about 300° for about 20 to about 300 minutes and removing water produced by vacuum distillation to form dehydrated phosphoric acid;
   (II) contacting
   (A) dehydrated phosphoric acid produced from step (I) with
   (B) an alkylsulfonic acid having 1 to 6 carbon atoms,
   under conditions of temperature and pressure to result in the absence of phosphoric/alkylsulfonic mixed anhydride and production of a mixture of alkylsulfonic acid and its corresponding anhydride at a conversion of at least 10% of said alkylsulfonic acid to the corresponding alkylsulfonic anhydride, and
   (III) separating the mixture of alkylsulfonic acid and its corresponding anhydride from phosphoric acid by distillation.

10. The process of claim 9 wherein the alkylsulfonic acid is methanesulfonic acid or 1,2-ethanesulfonic acid and step (II) is conducted at a pressure of less than about 1 mm Hg and a temperature of about 180° C. to about 300° C.

* * * * *